United States Patent [19]
Patel et al.

[11] Patent Number: 5,391,495
[45] Date of Patent: Feb. 21, 1995

[54] STEREOSELECTIVE REDUCTION OF KETONES

[75] Inventors: Ramesh N. Patel, Bridgewater, N.J.; Amit Banerjee, Yardley, Pa.; Clyde G. McNamee, Lawrenceville; Laszlo J. Szarka, East Brunswick, both of N.J.

[73] Assignee: Bristol-Myers Squibb Company, New York, N.Y.

[21] Appl. No.: 143,976

[22] Filed: Oct. 27, 1993

Related U.S. Application Data

[63] Continuation of Ser. No. 972,286, Nov. 5, 1992, abandoned.

[51] Int. Cl.$^6$ .......................... C12P 7/22; C12N 1/20; C12N 1/14
[52] U.S. Cl. ..................... 435/280; 435/911; 435/156; 435/931; 435/872; 435/254.1; 435/255.1; 435/252.1
[58] Field of Search ................. 435/280, 254.1, 255.1, 435/252.1, 911, 170, 156, 931, 872

[56] References Cited

U.S. PATENT DOCUMENTS

| | | |
|---|---|---|
| 3,342,584 | 9/1967 | Larsen et al. |
| 4,857,468 | 8/1989 | Kutsuki et al. |
| 5,106,736 | 4/1992 | Patel et al. |

OTHER PUBLICATIONS

Bradshaw, et al. "A Pseudomonas sp. Alcohol Dehydrogenase With Broad Substrate Specificity and Unusual Stereospecificity for Organic Synthesis," *J. Org. Chem.*, 57, 1526–1532, 1992.

Bradshaw, et al., "*Lactobacillus kefir* Alcohol Dehydrogenase: A Useful Catalyst for Synthesis," *J. Org. Chem.*, 57, 1532–1536, 1992.

Larsen, A. A. and Lish, P. M., "A New Bio-Isostere: Alkylsulphonamidophenethanolamines," *Nature*, 203, 1283–1284, 1964.

Lok, K. P., et al., "Enzymes in Organic Synthesis. 34. Preparations of Enantiomerically Pure Exo- and Endo-Bridged Bicyclic [2.2.1] and [2.2.2] Chiral Lactones via Sterospecific Horse Liver Alcohol Dehydrogenase Catalyzed Oxidations of Meso Diols," *J. Am. Chem. Soc.* 107(8), 2521–2526, 1985.

Ng. G. S. Y, et al., "Enzymes in Organic Synthesis–29. Preparations of Enantiomerically Pure cis-2,3- and 2,4-Dimethyl Lactones via Horse Liver Alcohol Dehydrogenase-catalyzed Oxidations," *Tetrahedron* 40(8), 1235–1243, 1984.

Bridges, A. J. et al., "Preparations of Enantiomerically Pure Bicyclic [3.2.1] and [3.3.1] Chiral Lactones via Stereospecific Horse Liver Alcohol Dehydrogenase Catalyzed Oxidations of Meso Diols," *J. Am. Chem. Soc.* 106(5), 1461–1467, 1984.

Fischli, A., "Chiral Building Blocks in Enantiomer Synthesis Using Enzymatic Transformations," *Mod. Synth. Methods, Conf. Pap. Int. Semin.*, 2nd., Rolf Scheffold (Ed), 269–350, 1980.

Lish, et al., "Pharmacological and toxicological Properties of Two New $\beta$-Adrenergic Receptor Antagonists," *J. Pharma. Exper. Ther.*, 149, 161–173, 1965.

Somani, P. and Bachand, T., "Blockade of Cardiac Effects of Isoproterenol by the Stereoisomers of Sotalol," *European Journal of Pharmacology*, 7, 239–247, 1969.

Akita, H., et al., "The Use of Microorganisms in Organic Synthesis.IV. Microbiological Asymmetric Reduction of Methyl 3-Phenyl 2-Oxybutyrate," *Chem. Pharm. Bull.* 32(4), 1342–1348, 1984.

(List continued on next page.)

*Primary Examiner*—Irene Marx
*Attorney, Agent, or Firm*—Thomas R. Savitsky

[57] ABSTRACT

The present invention concerns a process for the stereoselective enzymatic reduction of keto group-containing compounds such as N-(4-(2-chloroacetyl)-phenyl)methanesulfonamido to form the corresponding hydroxyl-group containing compound. The process is selective for the D(+) enantiomer and is catalyzed by enzymes such as oxido-reductase or dehydrogense, or by microorganisms such as Hansenula, Rhodococcus, or Norcardia species.

15 Claims, No Drawings

OTHER PUBLICATIONS

Hummel, W., "Enzyme-catalyzed Synthesis of Optically Pure R(+)-phenylethanol," *Biotechnol. Lett.* 12(6), 403–408, 1990.

Hummel, et al., "New Enzymes for the Synthesis of Chiral Compounds," *Ann. N.Y. Acad. Sci.,* 434, 194–205, 1984.

Whitlock, H. W., Jr., "Enzymatic Versus Chemical Synthesis of Molecules Labeled with Heavy Isotopes," *Tech. Chem. (N.Y.),* 10, 1045–1065, 1976.

Whitesides, et al., "The Use of Enzymes as Catalysts for Synthesis in Medicinal Chemistry: Chiral Synthons and Carbohydrates," *New Methods in Drug Research,* 2, 1–15, 1988.

Flynn, G. A. and Beight, D. W., "An Efficient Synthesis of Ethyl (R)-2-Hydroxy-4-Phenylbutyrate: A Useful Intermediate in the Synthesis of Converting Enzyme Inhibitors," *Tetrahedron Lett.* 29(4), 423–426, 1988.

Fuganti, C. and Servi, S., "Enzyme Mediated Synthesis of Pheromones," *Bioflavour '87, Proc. Int. Conf.,* Peter Schreier (Ed), 555–569, 1988.

Sonnet, P. E., "Enzymes for Chiral Synthesis," *Chemtech,* 18(2), 94–98, 1988.

Dodds, et al., "Enzymes in Organic Synthesis. 38. Preparations of Enantiometerically Pure Chiral Hydroxydecalones via Stereospecific Horse Liver Alcohol Dehydrogenase Catalyzed Reductions of Decalindiones," *J. Am. Chem. Soc.* 110(2), 577–583, 1988.

Battersby, A. R., "Enzymic Synthesis of Labeled Chiral Substances," *Ciba Found. Symp.,* 111, 22–30, 1985.

STEREOSELECTIVE REDUCTION OF KETONES

This application is a continuation of application Ser. No. 07/972,286, filed Nov. 5, 1992, now abandoned.

FIELD OF THE INVENTION

The present invention concerns the stereoselective microbial reduction of certain keto group-containing sulfonamido compounds to form the corresponding hydroxyl group-containing compounds.

BACKGROUND OF THE INVENTION

Larsen and Lish (Larsen, A. A. and Lish, P. M. (1964) Nature, 203, 1283–1284) reported the biological activity of a series of phenethanolamine bearing alkyl sulfonamido groups on the benzene ring. Within this series, some compounds possessed adrenergic and anti-adrenergic actions including alpha-adrenergic receptor block or receptor stimulation, beta-adrenergic receptor block or receptor stimulation. D-(+) sotalol is a beta-blocker (Uloth, R. H., Kirk, J. R., Gould, W. A., and Larsen, A. A. (1966) Sulfonanilides, 9, 88–96). Unlike other beta-blockers, it has class III antiarrhythmic properties (Lish, P. A., Weikel, J. H., and Dungan, K. W. (1965) J. Pharma. and Exper. Therapeutics, 149, 161–173). The beta-adrenergic blocking drugs such as propanolol and sotalol have been separated chemically into the dextro and levo rotatory optical isomers, and it has been demonstrated that the activity of the D(+) isomer is 50 times that of the corresponding L(−) isomer (Somani, P., and Bachand, T. (1969) Eur. J. Pharma, 7, 239–247). Thus, it would be highly desirable to have a facile stereoselective process for obtaining the enantiomeric pure isomers of the above described sulfonamido compounds.

The use of enzymes and microorganisms to produce certain optically active compounds is known in the art (see, for example, U.S. Pat. No. 5,106,736; U.S. Pat. No. 4,857,468; Akita, H. et al., (1984) Chem. Pharm. Bull., 32(4), 1342–1348; Hummel, W. (1990) Biotechnology Letters, 12(60), 403–408; and Schneider, M. P. et al., pp 483–529 in Bioflavour '87, P. Schreier, editor, De Grugter, Berlin (1988)). However, heretofore the stereoselective microbial/enzymatic reduction of certain keto group-containing compounds as hereinafter described has been unknown.

We have discovered the stereoselective microbial reduction of certain ketones such as N-(4-(2-chloroacetyl)phenyl)-methanesulfomamide to the corresponding (+)-alkanols. The alkanols are either biologically active themselves or are key chiral intermediates for the synthesis of certain cardiovascular drugs such as D-(+) sotalol.

SUMMARY OF THE INVENTION

The present invention provides a process for the stereoselective enzymatic reduction of keto group-containing compounds to form the corresponding hydroxyl group-containing compounds.

Specifically, the present invention provides a process for preparation of an optically active alkanol compound of the formula:

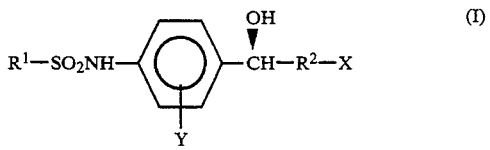

wherein
$R^1$ is lower alkyl, aryl, or substituted aryl;
$R^2$ is an alkylene group of 1 to 4 carbon atoms joining —X and

through from 1 to 2 carbon atoms;
Y is hydrogen, halogen, hydroxy, nitro, lower alkoxy, benzyloxy, substituted benzyloxy, lower alkyl, or $R^3SO_2NH$— wherein $R^3$, independently, has the same meaning as $R^1$; and
X is chloro, bromo, iodo, amino, monoalkylamino, dialkylamino, or the hydrochlorides of amino, monoalkylamino, or dialkylamino;
comprising
contacting a ketone compound of the formula

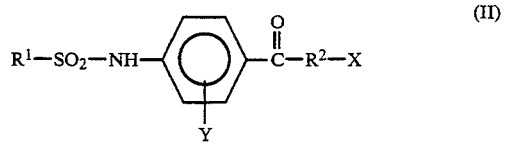

wherein $R^1$, X and Y are as previously defined, and
$R^2$ is an alkylene group of 1 to 4 carbon atoms joining —X and

through from 1 to 2 carbon atoms;
with an enzyme or microorganism capable of catalyzing the stereoselective reduction of the compound of Formula II to form the compound of Formula I.

DETAILED DESCRIPTION OF THE INVENTION

The compounds of Formula I are useful as beta-adrenergic blockers in therapeutic treatment of antianginal, antiarrhythmic and antihypertensive conditions or are intermediates useful for the preparation thereof (see, for example, U.S. Pat. No. 3,351,584).

The term "alkyl" or "alk" as used herein alone or as a part of another group, denotes such optionally substituted, but preferably unsubstituted, straight and branched chain saturated hydrocarbon groups, preferably having 1 to 10 carbons in the normal chain. Exemplary unsubstituted such groups include methyl, ethyl, propyl, isopropyl, n-butyl, iso-butyl, t-butyl, pentyl, hexyl, isohexyl, heptyl, 4,4-dimethyl, pentyl, octyl, 2,2,4-trimethyl pentyl, nonyl, decyl and the like. The alkyl groups may be substituted by appropriate substituents, that is, substituents providing compounds suitable for use in the present invention. Exemplary substituents of the alkyl group include one or more, preferably three or fewer, chloro groups, bromo groups, or iodo groups.

The terms "lower alk" or "lower alkyl" as used herein, denote such optionally substituted, but preferably unsubstituted, groups as described above for alkyl having 1 to 4 carbon atoms in the normal chain.

The term "lower alkoxy" denotes a lower alkyl group as described above bonded through an oxygen linkage (—O—). The terms "monoalkylamino" or "dialkylamino" denote an amino group substituted by one or two alkyl groups as described above, respectively.

The term aryl used herein denotes homocyclic aromatic groups, preferably containing 1 or 2 rings and 6 to 12 ring carbons. Exemplary aryl groups include phenyl, biphenyl, and naphthyl. The terms "substituted aryl" and "substituted benzyloxy" denote groups wherein the aromatic ring or rings are substituted. Exemplary substituents include one or more, preferably three or fewer, nitro groups, alkyl groups as described above or groups described above as substituents for the alkyl group.

The process of the present invention has the advantage of producing an enantiospecific result. The process primarily yields the D(+) enantiomer rather than a racemic mixture of preferred and unpreferred enantiomers. Additional advantages of particular embodiments include, for example, a single step enantiospecific reduction compared with multi-step chemical synthesis. Also, particularly, when the reduction is catalyzed at ambient temperature and pressure, one obtains high conversion of the ketone compound to the desired enantiomer of the corresponding alcohol compound, and high enantiomeric purity of the alcohol compound.

Enzymes and Microorganisms

The enzyme or microorganism employed in the present invention may be any enzyme or microorganism capable of catalyzing the stereoselective enzymatic reduction described herein. The enzymatic or microbial materials may be employed in the free state or immobilized on a support such as by physical absorption or entrapment.

Suitable enzymes, regardless of origin or purity, include those enzymes referred to as oxido-reductases or dehydrogenases. The enzyme employed may, for example, be an enzyme isolated from a microorganism such as by homogenizing cell suspensions, followed by disintegration, centrifugation, DEAE-cellulose chromatography, ammonium sulfate fractionation, chromatography using gel filtration media such as Sephacryl (cross-linked co-polymer of allyl dextran and N,N'-methylene bisacrylamide) chromatography, and ion exchange chromatography such as Mono-Q (anion exchanger which binds negatively charged biomolecules through quaternary amine groups) chromatography. Exemplary such enzymes include L-2-hydroxyisocaproate dehydrogenase, lactic acid dehydrogenase, yeast enzyme concentrate (Sigma), and beta-hydroxy butyrate dehydrogenase, or those enzymes derived from the microorganisms described hereinafter.

With respect to the use of microorganisms, the methods of the present invention may be carried out using any suitable microbial materials capable of catalyzing the stereoselective enzymatic reduction described herein. For example, the cells may be used in the form of intact wet cells or dried cells such as lyophilized, spray-dried or heat-dried cells, or in the form of treated cell material such as ruptured cells or cell extracts. Suitable microorganisms include genera from bacteria, yeasts and fungi such as Achromobacter, Acinetobacter, Actinomyces, Alkaligenes, Arthrobacter, Azotobacter, Bacillus, Brevibacterium, Corynebacterium, Flavobacterium, Methylomonas, Mycobacterium, Nocardia, Psuedomonas, Rhodococcus, Streptomyces, Xanthomonas, Aspergillus, Candida, Fusarium, Geotrichum, Hansenula, Kloeckera, Penicillum, Pichia, Rhizopus, Rhodotorula, Saccharomyces, Trichoderma, Mortierella, Cunninghamella, Torulopsis and Rhodopseudomonas.

Preferred microorganisms include *Arthrobacter simplex, Nocardia restricta, Nocardia salmonicolor, Rhodococcus fascians, Rhodococcus rhodochrous, Mycobacterium vacca, Nocardia meditteranei, Nocardia autotrophica, Rhodococcus equi, Candida albicans, Geotrichum candidum, Mortierella alpina, Pichia pastoris, Pichia methanolica, Cunninghamella echinalate, Torulopsis polysporium, Torulopsis glabrata*, and *Acinetobacter calcoaceticus*, and especially *Rhodococcus globerulus* (e.g. ATCC 21505), *Candida guilliermondii* (e.g., ATCC 20318), *Rhodococcus erythropolis* (e.g., ATCC 4277), *Saccharomyces cerevisiae* (e.g., ATCC 24702), *Pseudomonas putida* (e.g., ATCC 11172), *Mortierella rammanianna* (e.g., ATCC 38191), *Hansenula fabiana* (e.g., ATCC 58045), *Hansenula polymorpha* (e.g., ATCC 26012), *Trichoderma polysporium* (e.g., ATCC 28014), Rhodococcus species (e.g., ATCC 21243, ATCC 12975, and ATCC 29675), *Rhodococcus fascians* (e.g., ATCC 21950), *Rhodococcus equi* (e.g., ATCC 14887), *Aureobasidium pullulans* (e.g., ATCC 16623), *Mucor hiemalis* (e.g., ATCC 89778), and *Mortierella alpina* (e.g., ATCC 36965).

The use of genetically engineered organisms is also contemplated. The host cell may be any cell, e.g., *Escherichia coli*, modified to contain a gene or genes for expressing one or more enzymes capable of catalysis as described herein.

It is particularly preferred to employ microorganisms of the genus Hansenula, particularly the species *Hansenula polymorpha*, especially the strain *Hansenula polymorpha* ATCC 26012, the species *Hansenula fabiana*, especially the strain *Hansenula fabiana* ATCC 58045, the genus Rhodococcus, especially Rhodococcus sp, ATCC 21243 and the species *Rhodococcus fascians*, ATCC 21950, and the genus Nocardia. The term "ATCC" as used herein refers to the accession number of the American Type Culture Collection, 12301 Parklawn Drive, Rockville, Md. 20852, the depository for the organism referred to. It is also particularly preferred to employ cell extracts or isolated enzymes from these organisms. Of course, combinations of two or more enzymes and/or microorganisms are contemplated to be within the scope of the invention.

The stereoselective enzymatic reduction method of the present invention may be carried out subsequent to the fermentation of the microorganism employed (two-stage fermentation and reduction), or concurrently therewith, that is, in the latter case, by in situ fermentation and reduction (single-stage fermentation and reduction). In the single-stage process, the microorganisms may be grown in an appropriate medium until sufficient growth of the microorganisms is attained. A compound of Formula II may then be added to the microbial cultures and the stereoselective enzymatic reduction continued with the fermentation, preferably until complete conversion is obtained.

In the two-stage process, the microorganisms may, in the first stage, be grown in an appropriate medium for fermentation until exhibiting the desired enzymatic (e.g., oxido-reductase) activity. Subsequently, the cells may be harvested by centrifugation and microbial cell suspensions prepared by suspending harvested cells in an appropriate buffered solution. Buffers such as tris-HCl, phosphates, sodium acetate and the like may be used. Water may also be used to prepare suspensions of microbial cells. In the second stage, the compound of Formula II may be mixed with the microbial cell suspensions, and the stereoselective enzymatic reduction of the compound catalyzed by the microbial cell suspensions. The reduction is preferably conducted until all or nearly all of the compound of Formula II is stereoselectively reduced.

Growth of the microorganisms may be achieved by one of ordinary skill in the art by the use of an appropriate medium. Appropriate media for growing microorganisms include those which provide nutrients necessary for the growth of the microbial cells. A typical medium for growth includes necessary carbon sources, nitrogen sources, and trace elements. Inducers may also be added. The term "inducer", as used herein, includes any compound enhancing formation of the desired enzymatic (e.g. oxido-reductase) activity within the microbial cell, such as those compounds containing keto groups. Formula I compounds may be added as inducers during growth of the microorganism.

Carbon sources may include sugars such as maltose, lactose, glucose, fructose, glycerol, sorbitol, sucrose, starch, mannitol, propylene glycol, and the like; organic acids such as sodium acetate, sodium citrate, and the like; amino acids such as sodium glutamate and the like; and alcohols such as ethanol, propanol and the like.

Nitrogen sources may include N-Z amine A, corn steep liquor, soy bean meal, beef extracts, yeast extracts, molasses, baker's yeast, tryptone, nutrisoy, peptone, yeastamin, sodium nitrate, ammonium sulfate and the like.

Trace elements may include phosphates and magnesium, manganese, calcium, cobalt, nickel, iron, sodium and potassium salts.

The medium employed may include more than one carbon or nitrogen source or other nutrient.

Preferred media include aqueous media containing the following (in weight %):

| Medium 1 | |
|---|---|
| Malt Extract | 1% |
| Yeast Extract | 1% |
| Peptone | 1% |
| Glucose | 2% |
| | pH 7.0 |
| Medium 2 | |
| Peptone | 0.3% |
| Glycerol | 4% |
| Malt Extract | 1% |
| Yeast Extract | 1% |
| | pH 7.0 |
| Medium 3 | |
| Sodium Succinate | 2% |
| Malt Extract | 1% |
| Yeast Extract | 1% |
| Peptone | 0.3% |
| | pH 7.0 |

The pH of the medium is preferably adjusted to about 6 to 8, most preferably to 6.5, sterilized, e.g. at a temperature of 121° C. for 30 minutes, and then adjusted to a pH of about 6.5 to 7.5, preferably 7.0, after sterilization.

The process of the present invention is performed under conditions suitable for forming the desired compound of Formula I. The pH of the medium is preferably maintained between 4.0 and 9.0, most preferably between 6.0 and 8.0, during the growth of microorganisms and during the stereoselective reduction process whether performed with enzymes or microorganisms.

Temperature is a measure of the heat energy available for the stereoselective reduction process, and should be maintained to ensure that there is sufficient energy available for this process. A suitable temperature range for the process of the invention is from about 15° C. to about 60° C. A preferred temperature range is from about 25° to about 40° C.

Pressure is not known to be critical to practice of the invention and for convenience about atmospheric pressure is typically employed.

The process of the invention is preferably carried out under aerobic conditions. The agitation and aeration of the reaction mixture affects the amount of oxygen available during the stereoselective reduction process, which may be conducted, for example, in shake-flask cultures or fermentor tanks during growth of microorganisms in a single-stage or two-stage process. The agitation range from 50 to 1000 RPM is preferable, with 50 to 500 RPM being most preferred. Aeration of about 0.1 to 10 volumes of air per volume of media per minute (i.e., 0.1 to 10 v/vt) is preferred, with aeration of about 5 volumes of air per volume of media per minute (i.e., 5 v/vt) being most preferred.

Complete conversion of the compound of Formula II may take, for example, from about 4 to 48 hours, preferably 12 to 24 hours, measured from the time of initially treating the compound of Formula II with a microorganism or enzyme as described herein.

The stereoselective enzymatic reduction method of the present invention may be carried out using a co-factor such as nicotinamide adenine dinucleotide (NADH), especially when an isolated enzyme is employed. NADH, for example, may thereafter be regenerated and reused. A further enzyme that regenerates the NADH in situ may be employed such as formate dehydrogenase. Suitable hydrogen donors include molecular hydrogen, a formate (e.g. an alkali metal or ammonium formate), a hypophosphite or an electrochemical reduction in the presence of a viologen, for example methyl viologen. It is also possible to regenerate NADH without further enzymes using, for example, ethanol or formate.

It is preferred to employ an aqueous liquid as the reaction medium, although an organic liquid, or a miscible or immiscible (biphasic) organic/aqueous liquid mixture may also be employed.

It is preferred to employ 0.1 to 25 weight % of the compound of Formula II starting material based on the combined weight of the compound and reaction medium. The amount of enzyme or microorganism employed relative to the starting material is selected to allow catalysis of the stereoselective enzymatic reduction of the present invention.

It is preferred to employ conditions providing a reaction yield greater than about 80%, most preferably greater than about 90%, and an optical purity of the D(+) enantiomer of about 60% or greater, preferably greater than about 80%, more preferably greater than about 90%, and most preferably greater than about 99%.

Groups, such as hydroxyl groups, on the compound of Formula II may optionally be protected for use in the stereoselective enzymatic reduction method of the present invention; such groups may optionally thereafter be deprotected.

Separation

The products of the stereoselective reduction process of the present invention may be isolated and purified by known methodologies such as by extraction, distillation, crystallization, column chromatography, and the like.

A preferred method for separating the desired compound of Formula I from the remaining compounds of the reaction medium is by extraction. An exemplary extraction technique, such as where product is prepared by whole cell suspensions, is that where the reaction medium, containing the aforementioned suspensions, is extracted with ethyl acetate, the organic layer is washed with brine, and the solvent is then removed under reduced pressure to generate an oily liquid which is chromatographed on a preparative HPLC using a C18 (25$\mu$) national column (2×10 inch) to produce the desired product(compound of Formula I).

The following examples are to illustrate the invention but should not be interpreted as a limitation thereon.

EXAMPLE 1

Stereoselective Enzymatic Reduction: Use of Various Strains of Whole Cells

The substrate for the following enzymatic reduction process was N-(4-(1-oxo-2-chloroethane)methane)sulfonamide (compound A) having the structure as follows.

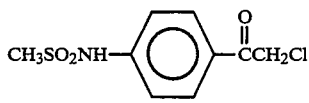

The desired product (compound B) was the compound having the formula:

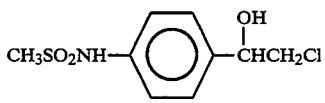

and the name (+)N-(4-(1-hydroxy-2-chloroethane)methane)sulfonamide. The microorganisms which were employed in the reduction process are listed in Table 1 which follows.

The microorganisms employed were maintained in a vial in liquid nitrogen. For routine development of inoculum, one vial was inoculated into 100 ml of Medium 1 (see above for the composition thereof) in a 500 ml flask and incubated at 28° C. and 280 RPM on a shaker for 48 hours. After growth of the microorganism, 10 ml of culture was inoculated into a 500 ml flask containing 100 ml of Medium 1 and incubated at 28° C. and 250 RPM on a shaker.

Cells were harvested and suspended in 100 mM potassium phosphate buffer pH 6.0. Ten ml of 20% w/v cell-suspensions were prepared. Cell-suspensions were supplemented with 25 mg of substrate (Compound A) and 750 mg of glucose and the reductions ("biotransformations") were conducted at 28° C., 150 RPM for 22–40 hours. One volume of sample was taken and extracted with two volumes of ethyl acetate and the separated organic phase was filtered through a 0.2 $\mu$m LID/x filter and collected.

Samples were analyzed for substrate and product concentration by a Hewlett Packard gas chromatogram with a flame ionization detector (FID). A Hewlett Packard (Palo Alto, California) fused silica capillary column (cross-linked methyl silicone, 15 m long, 0.33 $\mu$m film thickness, 0.32 mm I.D.) at 250° C. detector temperature, and 190° C. injection temperature was used. The initial oven temperature was 195° C. and final temperature was 205° C. Temperature was increased at 0.5° C./Min. Helium was used as a carrier gas at 50 ml/min. The retention time for substrate (Compound A) was 1.02 min and the corresponding reduced product (Compound B) was 9.6 min. The optical purity of product (Compound B) was determined by chiral HPLC. A Baker-bond Chiralcel OB column was used at ambient temperature. Injection volume was 20 $\mu$l, mobile phase was 65% hexane containing 35% n-butanol, flow rate was 0.5 ml/min, and detector wavelength was 230 nm. The retention time was 16.32 min for the R-(+) enantiomer and 13.63 min for the S-(−) enantiomer.

The results obtained by using various microorganisms grown on Medium 1 and following the above 15 procedure are shown in Table 1.

TABLE 1

| Microbial Reduction of Compound A to Compound B | | | |
|---|---|---|---|
| Microorganism | Reaction Time (hours) | (%) | Optical Purity of Compound B (%) |
| Aureobosidium pullulans ATCC 16623 | 48 | 73 | 75 |
| Hansenula polymorpha ATCC 26012 | 20 | 95 | 99 |
| Mucor hiemalis ATCC 8977b | 48 | 34 | 70 |
| Mortierella alpina ATCC 36965 | 20 | 35 | 80 |
| Trichoderma polysporium ATCC 28014 | 20 | 86 | 77 |
| Rhodococcus erythropolis ATCC 4277 | 20 | 63 | 68 |
| Rhodococcus sp. ATCC 12975 | 22 | 44 | 60 |
| Rhodococcus sp. ATCC 29675 | 22 | 53 | 95 |
| Rhodococcus sp. ATCC 21243 | 22 | 64 | 97 |
| Rhodococcus fascians ATCC 21950 | 22 | 45 | 99 |
| Rhodococcus oloberulus ATCC 21505 | 22 | 63 | 78 |
| Rhodococcus equi ATCC 14887 | 22 | 75 | 85 |

EXAMPLE 2

Use of Whole Cells: Variation in Reaction Time

The substrate for this process was Compound A and the desired product Compound B as described in Example 1.

Cells of Hansenula polymorpha ATCC 26012 were grown in 100 ml of Medium 1 combined in 500 ml flasks. Growth was carried out at 25° C. for 48 hours at 280 RPM. 100 ml of cultures were inoculated into 15L of Medium 2 (see above for the composition thereof) combined in a fermentor. Growth in the fermentor was carried out at 25° C., 15 liters per minutes (LPM) aeration and 500 RPM agitation for 60 hours. Cells were harvested from the fermentor and used for the reduction ("biotransformation") of Compound A to Compound B.

Cells (200 grams) were suspended in 3 liter of 100 mM potassium phosphate buffer, pH 6.0 and homogenous cell suspensions were prepared. 12 grams of Compound A and 120 grams of glucose were added to the cell suspensions and the biotransformation of Compound A to Compound B was carried out at 22° C., 160 RPM for 24 hours. After 24 hours, an additional 35 grams of glucose were added and the biotransformation was continued for 72 hours at 22° C., 160 RPM. Samples were prepared and product yield and optical purity were determined as described in Example 1. The results obtained were summarized in Table which follows.

TABLE 2

| Reaction Time | Yield of Compound B (%) | Optical Purity of Compound B (%) |
|---|---|---|
| 6 | 28 | — |
| 12 | 52 | — |
| 18 | 78 | — |
| 22 | 96 | 99 |

EXAMPLE 3

Use of Cell Extracts and Co-factor

The substrate for this process (Compound A) and the desired product (Compound B) were those described in Example 1.

Cells of *Hansenula polymorpha* ATCC 26012 were grown on Medium 1 and Medium 2 as described in Example 2.

Cells (150 grams) were suspended in 1.5L of 0.2M potassium phosphate buffer, pH 6.0. The homogenized cell suspensions were disintegrated at 4° C. by a Microfluidizer at 13,000 psi pressure. The disintegrated cell suspension was centrifuged at 12,000 RPM for 30 minutes. The clear supernatant ("cell extract") was used for the biotransformation of Compound A to Compound B.

One liter of cell extract was supplemented with 2.5 grams of substrate (Compound A), formate dehydrogenase (500 units), 0.7 mM NAD (nicotinamide adenine dinucleotide), and 25 grams of sodium formate. The reaction was carried out in a pH stat at pH 6.0, 150 RPM agitation, and 22° C. Periodically, samples were taken and analyzed for the reaction yield and optical purity of Compound B as described in Example 1. The results obtained are those shown in Table 3 which follows.

TABLE 3

| Reaction Time (hours) | Compound B g/L | Yield (%) | Optical Purity (%) |
|---|---|---|---|
| 24 | 2.3 | 90 | 99 |

In the above procedure, the NADH cofactor used for the biotransformation of Compound A to Compound B was, concurrent with the biotransformation, formed and regenerated using formate dehydrogenase, NAD+, and formate as shown below.

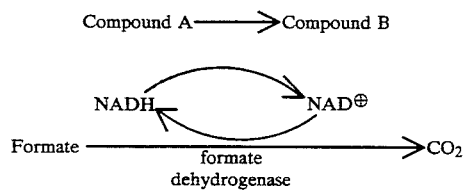

After complete conversion of Compound A to Compound B, the reaction mixture was adjusted to p 7.0 and extracted three times with equal volumes of ethyl acetate. The organic phase was separated and washed twice with 0.7M sodium bicarbonate. The separated organic layer was dried over anhydrous sodium sulfate and ethyl acetate was removed under reduced pressure. The resulting oily residue was dried under vacuum at room temperature to recover a pale white solid in 85% yield (isolated) and 99% optical purity.

We claim:

1. A process for preparation of an optically active alkanol compound of the formula:

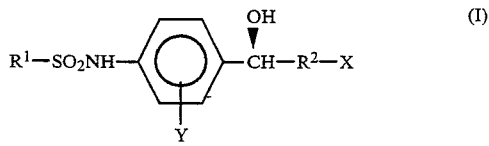

wherein
$R^1$ is lower alkyl or aryl;
$R^2$ is an alkylene group of 1 to 4 carbon atoms joining —X and

through from 1 to 2 carbon atoms;
Y is hydrogen, halogen, hydroxy, nitro, lower alkoxy, benzyloxy, lower alkyl, or $R^3SO_2NH$— wherein $R^3$, independently, has the same meaning as $R^1$; and
X is chloro, bromo, iodo, amino, monoalkylamino, or dialkylamino,k or the hydrochloride of amino, monoalkylamino, or dialkylamino;
comprising
contacting a ketone compound of the formula

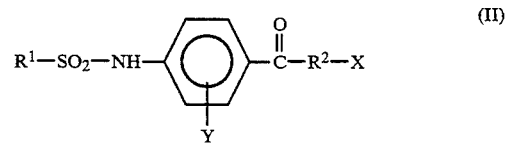

wherein $R^1$, X and Y are as previously defined, and
$R^2$ is an alkylene group of 1 to 4 carbon atoms joining —X and

through from 1 to 2 carbon atoms;
with a microorganism capable of catalyzing the stereoselective reduction of the compound of Formula II to form the compound of Formula I wherein said microorganism is selected from the group consisting of *Aureobasidium pullulans* ATCC 16623, *Hansenula polymorpha* ATCC 26012, *Mucor hiemalis* ATCC 8977, *Mortierella alphina* ATCC 36965, *Trichoderma polysporium* ATCC 28014, *Rhodococcus erythropolis* ATCC 4277, Rhodococcus sp. ATCC 12975, Rhodococcus sp. ATCC 29675, Rhodococcus sp. ATCC 21243, *Rhodococcus fascians* ATCC 21950, *Rhodococcus globerulus* ATCC 21505, and *Rhodococcus equi* ATCC 14887;
followed by the additional step of separating the compound of formula I.

2. The process of claim 1 catalyzed by a microorganism selected from the group consisting of *Rhodococcus globerulus* ATCC 21505, *Rhodococcus erythropolis* ATCC 4277, *Hansenula polymorpha* ATCC 26012, *Trichoderma polysporium* ATCC 28014, Rhodococcus sp. ATCC 21243, *Rhodococcus fascians* ATCC 21950, *Rhodococcus equi* ATCC 14887, *Aureobasidium pullulans* ATCC 16623, *Mortierella alpina* ATCC 36965, Rhodococcus sp. ATCC 12975, and Rhodococcus sp. ATCC 29675.

3. The process of claim 1 catalyzed by a microorganism selected from the group consisting of *Hansenula polymorpha* ATCC 26012, Rhodococcus sp. ATCC 21243, and *Rhodococcus fascians* ATCC 21950.

4. The process of claim 1 wherein $R^1$ is lower alkyl or phenyl, $R^2$ is ethylene or methylene, Y is hydrogen or lower alkyl, and X is chloro or isopropylamino hydrochloride.

5. The process of claim 1 wherein $R^1$ is methyl, $R^2$ is methylene, Y is hydrogen, and X is chloro.

6. The process of claim 1 carried out as a one-stage fermentation.

7. The process of claim 1 carried out as a two-stage fermentation.

8. The process of claim 1 carried out in the presence of an inducer.

9. The process of claim 1 carried out in a medium having one or more carbon sources selected from the group consisting of maltose, lactose, glucose, fructose, glycerol, sorbitol, sucrose, starch, mannitol, propylene glycol, sodium acetate, sodium citrate, sodium glutamate, ethanol, propanol; one or more nitrogen sources selected from the group consisting of N-Z amine A, corn steep liquor, soy bean meal, beef extracts, yeast extracts, molasses, baker's yeast, tryptone, nutrisoy, peptone, yeastamin, sodium nitrate, ammonium sulfate; and one or more trace elements selected from the group consisting of phosphates, manganese, calcium, cobalt, nickel, iron, sodium salts and potassium salts.

10. The process of claim 1 carried out at a pH of about 4 to about 9 and at a temperature of about 15° C. to about 60° C.

11. The process of claim 1 carried out at a pH of about 6 to about 8, at a temperature of about 25° C. to about 40° C., and for 4 to 48 hours.

12. The process of claim 1 carried out under agitation.

13. The process of claim 1 wherein the separating step is carried out by extraction, distillation, crystallization, or column chromatography.

14. The process of claim 1 having a reaction yield of greater than about 80%, and an optical purity of the compound of Formula I of greater than about 80%.

15. The process of claim 1 having a reaction yield of greater than about 90%, and an optical purity of the compound of Formula I of greater than about 90%.

* * * * *